(12) United States Patent
Mogul

(10) Patent No.: US 7,122,020 B2
(45) Date of Patent: Oct. 17, 2006

(54) LINKAGE STEERING MECHANISM FOR DEFLECTABLE CATHETERS

(75) Inventor: Jamil Mogul, San Jose, CA (US)

(73) Assignee: Mogul Enterprises, Inc., San Jose, CA (US)

( * ) Notice: Subject to any disclaimer, the term of this patent is extended or adjusted under 35 U.S.C. 154(b) by 0 days.

(21) Appl. No.: 11/166,885

(22) Filed: Jun. 24, 2005

(65) Prior Publication Data

US 2005/0288627 A1    Dec. 29, 2005

Related U.S. Application Data

(60) Provisional application No. 60/582,772, filed on Jun. 25, 2004.

(51) Int. Cl.
*A61M 37/00*    (2006.01)
(52) U.S. Cl. .................... 604/95.04; 604/146
(58) Field of Classification Search ............. 604/95.04; 600/146
See application file for complete search history.

(56) References Cited

U.S. PATENT DOCUMENTS 3,091,235 A * 5/1963 Richards .................... 600/142
5,336,182 A * 8/1994 Lundquist et al. .......... 604/528

* cited by examiner

*Primary Examiner*—Nicholas D. Lucchesi
*Assistant Examiner*—Laura A. Bouchelle
(74) *Attorney, Agent, or Firm*—Buchanan Ingersoll & Rooney PC

(57) ABSTRACT

A dual 4-bar linkage steering mechanism consists of four strip/rod-like prismatic or disk/sphere-like revolute side links, called, side link 1A, side link 1B, side link 2A and side link 2B; two strip/rod-like prismatic coupler links, called, coupler link A, coupler link B; and a common fixed link. In one option, the side link 1A and the side link 1B are integrated to act as a whole, and side link 2A and the side link 2B are also integrated to act as a whole. In other option, the side link 1A and the side link 1B are separate and move independently, and the side link 2A and the side link 2B are also separate and move independently. The coupler link A and coupler link B are either rigid or flexible.

15 Claims, 17 Drawing Sheets

Dual 4-bar Linkage Steering Mechanism in Handle Half with A Built-in Fixed Link

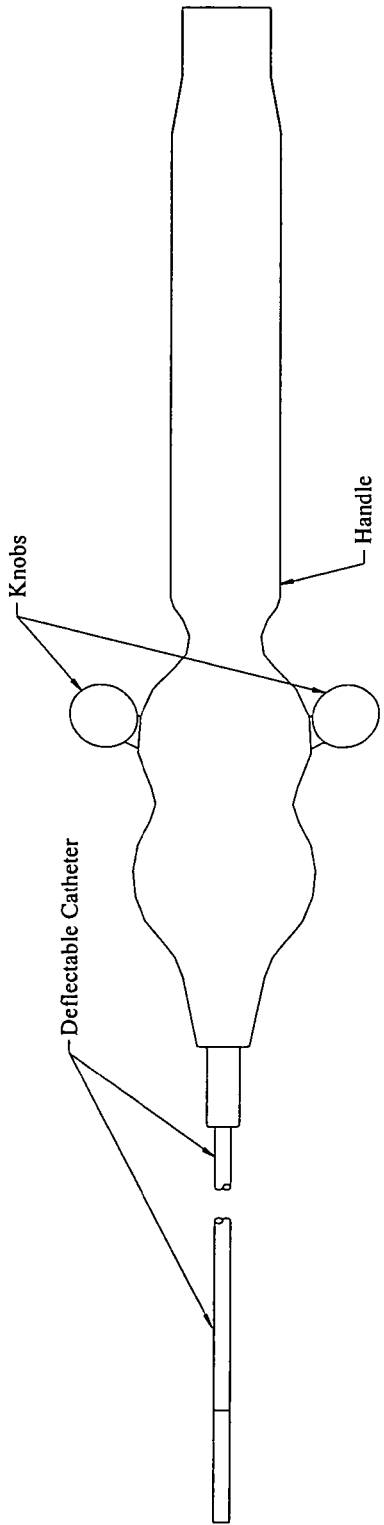
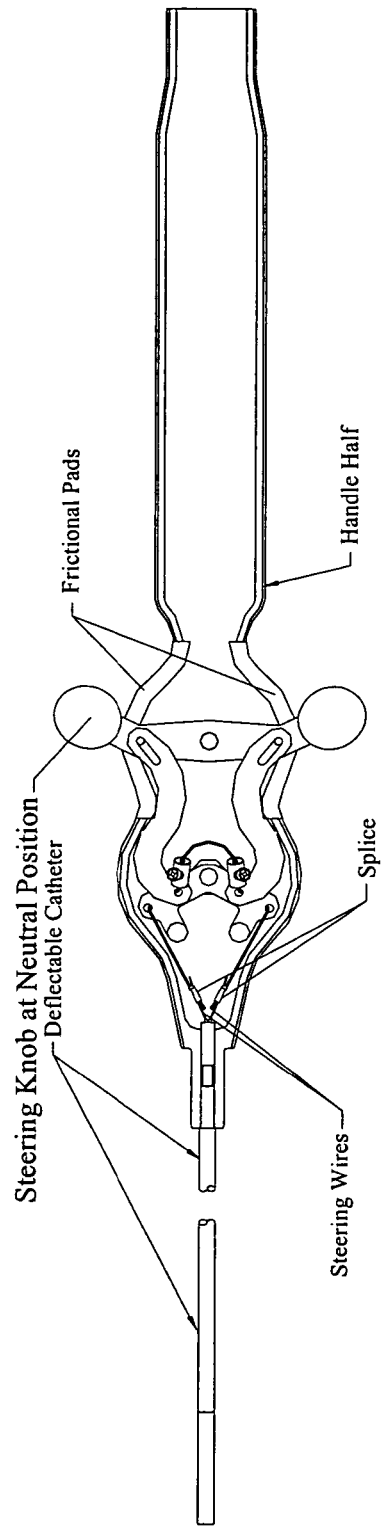
FIG. 1 Linkage Steering Mechanism in Handle with Catheter
FIG. 2 Dual 4-bar Linkage Steering Mechanism in Handle Half with A Built-in Fixed Link Dual 4-bar Linkage Steering Mechanism with Flexible Cable, Clamp & without the Fixed Link Dual 4-bar Linkage Steering Mechanism with Integral Side Links Dual 4-bar Linkage Steering Mechanism with Individual Side Links Dual 4-bar Linkage Steering Mechanism with Integral Side Links & A Fixed Link Dual 4-bar Linkage Steering Mechanism with Individual Side Links & A Fixed Link Steering Knob at 45° Position Steering Knob at 45° Position Dual 4-bar Linkage Steering Mechanism in Handle Half with A Built-in Fixed Link, Showing Catheter Deflection Dual 4-bar Linkage Steering Mechanism with A Flexible Coupler in Handle Half

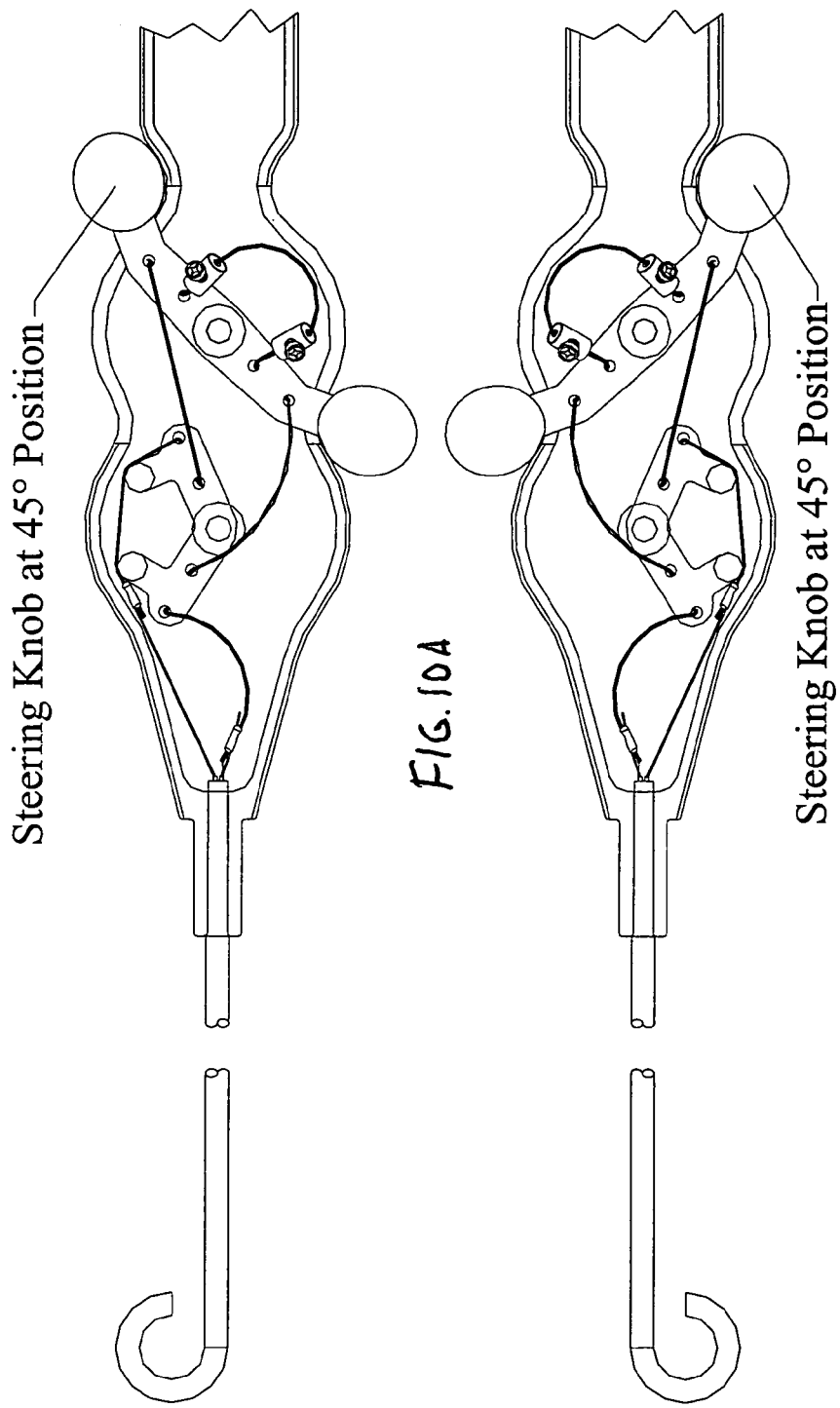
FIG. 10A — Steering Knob at 45° Position
FIG. 10B — Steering Knob at 45° Position
Dual 4-bar Linkage Steering Mechanism with A Flexible Coupler in Handle Half, Showing Catheter Deflection Multiple Linkage for High Travel-output in Handle Half Multiple Linkage for High Travel-output High Travel-output Linkage Steering Steering Mechanism with Dual Lever in Handle Half High Travel-output Linkage Steering Steering Mechanism for Bi-directional Steering in Handle Half High Travel-output Linkage Steering Steering Mechanism for Bi-directional Steering

Another Option: A Lever with Studs to Increase the Travel-output of A Lever Type Steering Mechanism

Variable Frictional Force with Spring-loaded Washer

LINKAGE STEERING MECHANISM FOR DEFLECTABLE CATHETERS

PRIORITY CLAIM

This application claims priority to U.S. Provisional Patent Application No. 60/582,772, filed Jun. 25, 2004, entitled "Dual Linkage Steering Mechanism for a Deflectable Catheter.

SUMMARY

A rotationally-actuated mechanism having two integral 4-bar linkages is installed in the handle of a deflectable catheter containing at least two mechanical wires, each of which is attached to the mechanism at one end and connected to the catheter's distal tip at the other end. When actuated, the mechanism deflects the distal tip in one direction from the tip's straight position to an arc angle in a plane by pulling one of the wires. The reverse actuation of the mechanism brings the tip back to the straight position while a further reverse actuation deflects the tip in an opposite direction to an arc angle in the same plane by pulling the other wire.

The mechanism is a function generation linkage whose movable links are made longitudinally proportional to have a variable relative motion ratio, which plays a key role in the functional aspect of the mechanism. A high relative motion ratio of the driven link to the drive link helps achieve a large deflection angle of the distal tip with a very small rotational actuation of the mechanism.

On either side of the handle is a compliant pad where the drive link member extends out and makes a frictional contact with the pad that holds the link in any position within the mechanism actuation range. The friction-held link maintains the tension in the pull wire deflecting the distal tip and thereby locks the tip curve shape in place. Alternatively, to hold the link for locking a tip-curve shape, on either side of the pin or the integral spindle of the drive link is a complaint washer (with or without a helical spring) that is in a frictional contact between the handle and the link. To have a variable frictional force, one end of the spindle is threaded and inserted into the corresponding threaded hole in the handle.

Either end of the drive link has an integral plastic component, which acts as a knob for the user to actuate the mechanism to deflect the distal tip. The shape of the handle and the organically-shaped knob including the knob's location on the handle are designed to be ergonomically acceptable.

PROBLEM TO BE SOLVED

Because of their inherent design limitations due to geometric configurations, dimensional constraints, material's mechanical/thermal properties, installed structures/components and fabrication/assembly methods, certain deflectable catheters require 0.5 inch to 1.0 inch of travel of the their pull wires to achieve a distal-tip deflection angle of 270 degrees in one direction for uni-directionally steerable catheter. This means if the steering mechanism has no designed-in mechanical advantage, the actuation distance of the mechanism's actuator (that is often a knob operated by the user) has to be from 0.5 inch to 1.0 inch. But if the catheter's tip is to be deflected in two directions for bi-directionally steerable catheters then the total actuation distance will be from 1.0 inch to 2.0 inches, which is ergonomically not acceptable by the users who often operate the mechanism for several hours with one hand using their thumb.

So, to address the ergonomic concern, the deflectable catheters that have inherent design limitations are offered with a distal-tip deflection angle of less than 180 degrees for uni-directionally steerable catheters and less than 150 degrees for bi-directionally steerable catheters. These catheters will be acceptable for some clinical procedures, but for other clinical procedures, physicians will still need deflectable catheters, which have a distal-tip deflection angle of 210 to 270 degrees.

Without changing the catheter shaft design of a deflectable catheter which has inherent design limitations, this dual linkage steering mechanism, attached to the catheter, is able to deflect the catheter's distal-tip to an angle of 270 degrees and even beyond with multiple side linkage.

IN THE DRAWINGS

FIG. 1 is a side elevational view of a linkage steering mechanism in accordance with the present invention;

FIG. 2 is a longitudinal cross-sectional view showing a dual 4-bar linkage steering mechanism in accordance with the present invention;

FIGS. 9–10B are longitudinal cross-sectional views showing an alternative embodiment of a linkage steering mechanism in accordance with the present invention;

OBJECT OF INVENTION

Figure 3:
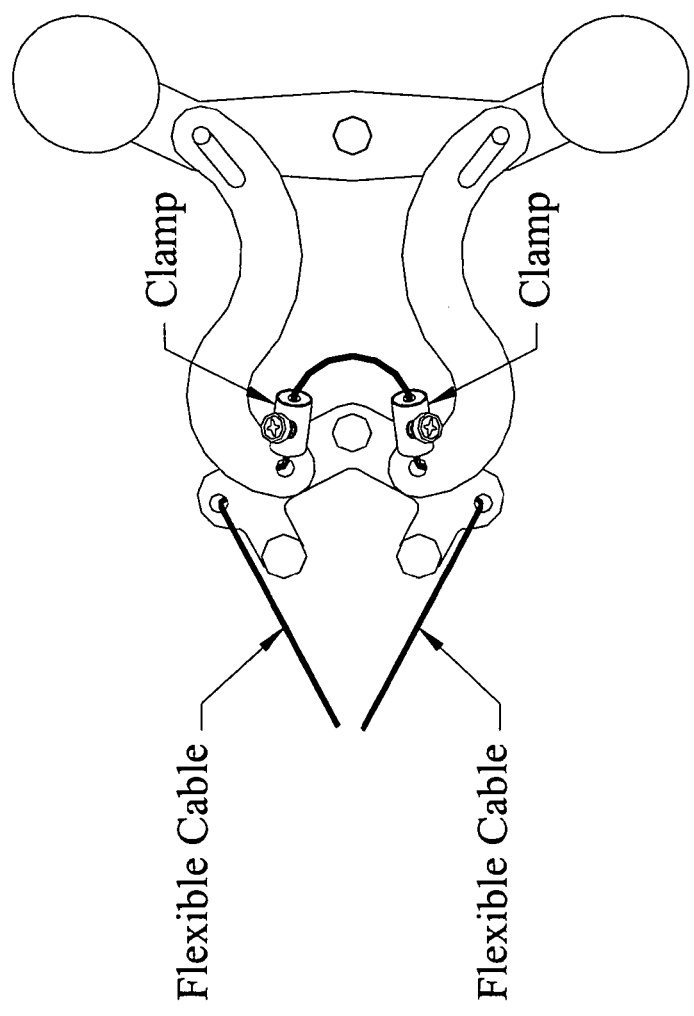
FIGS. 3–8B are longitudinal cross-sectional views showing variations of the dual 4-bar linkage steering mechanism of FIG. 2.
Figure 4:
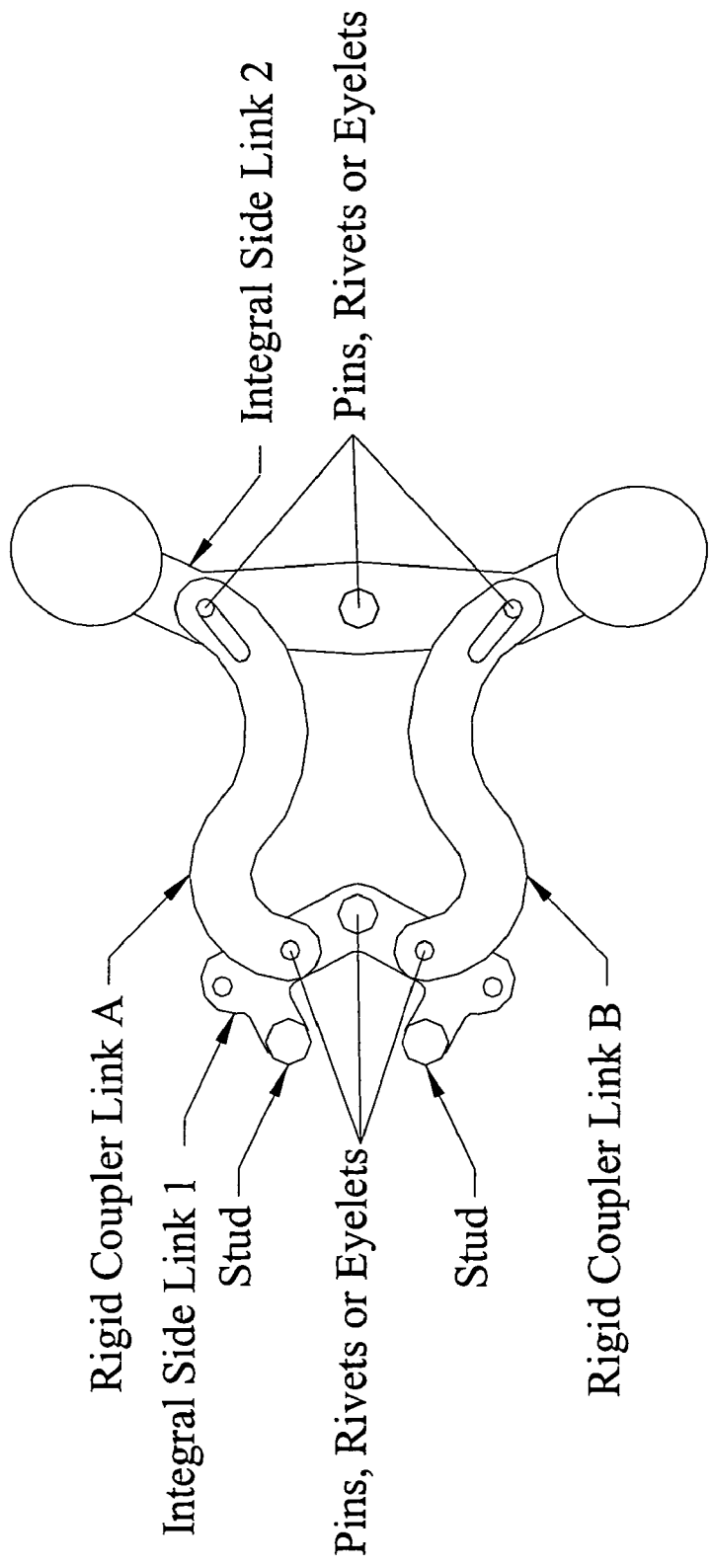
Figure 5:
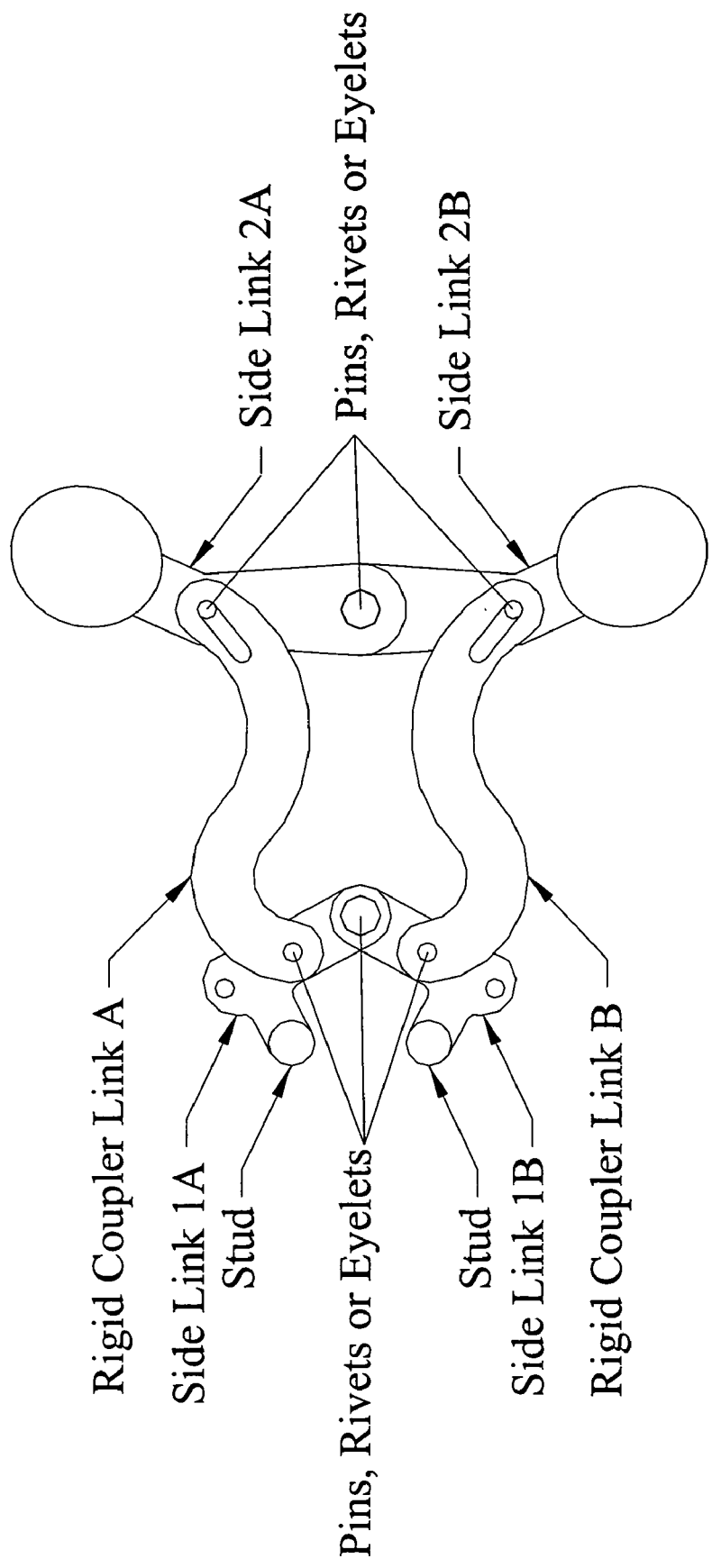
Figure 6:
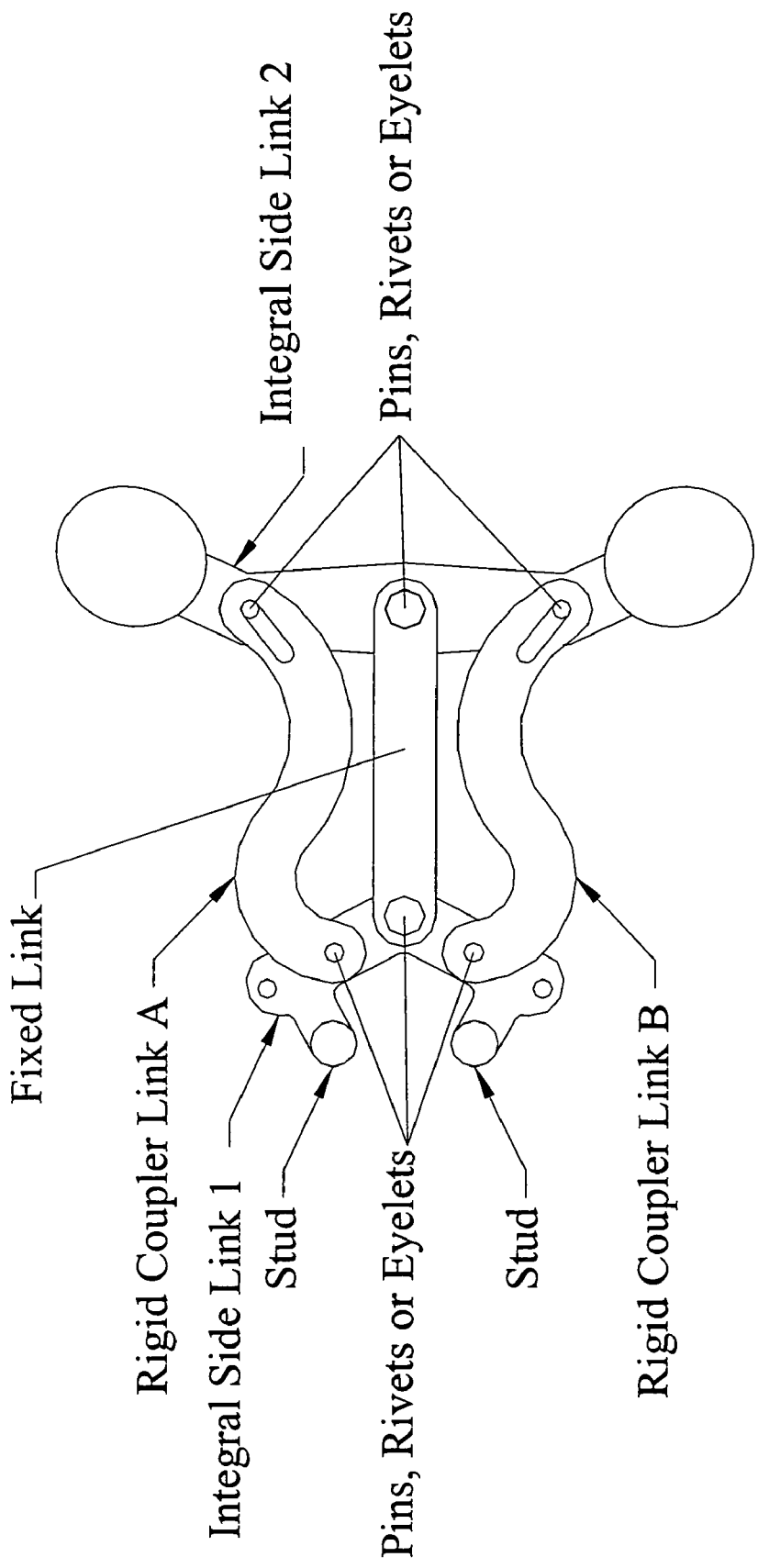
Figure 7:
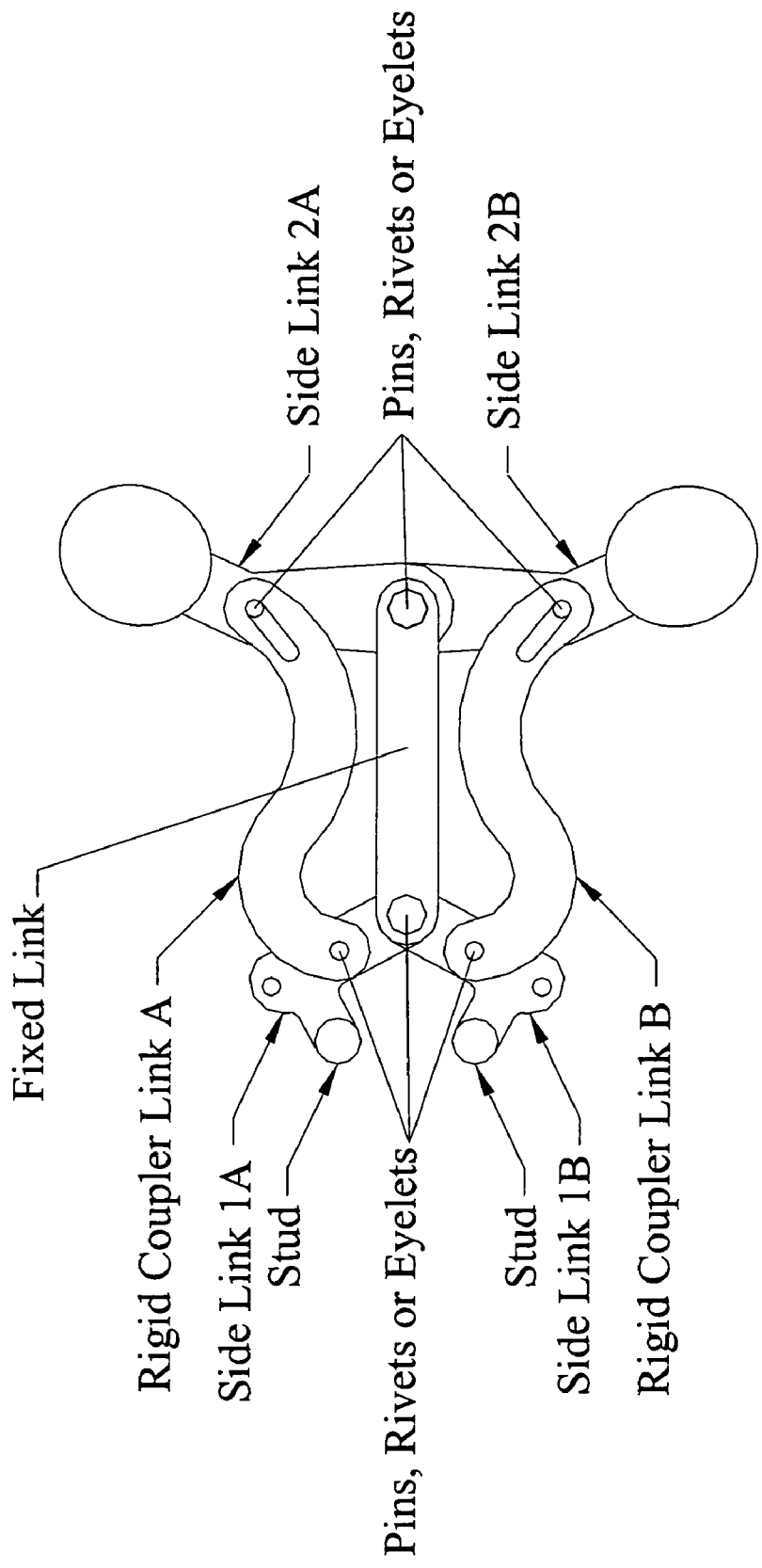
Figure 8A:
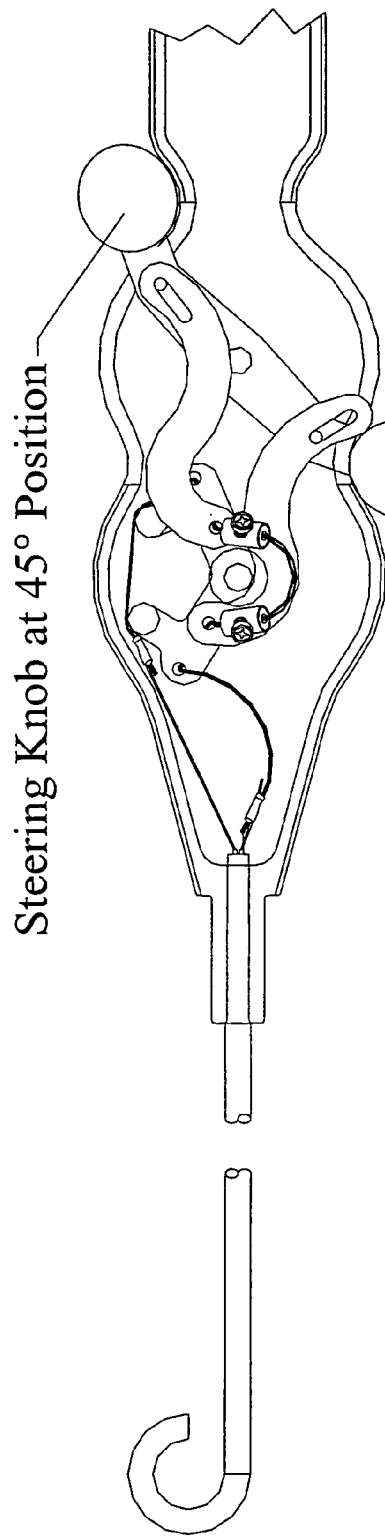
Figure 8B:
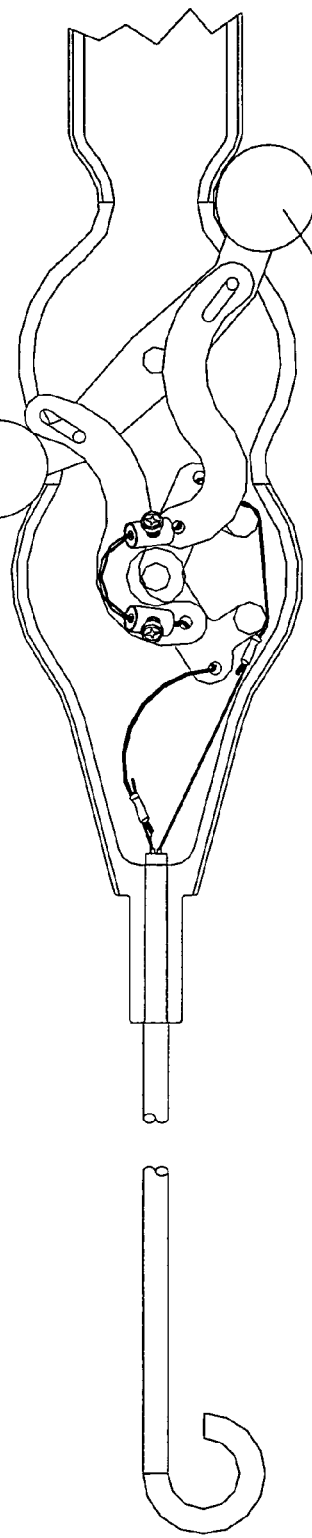
Figure 9:
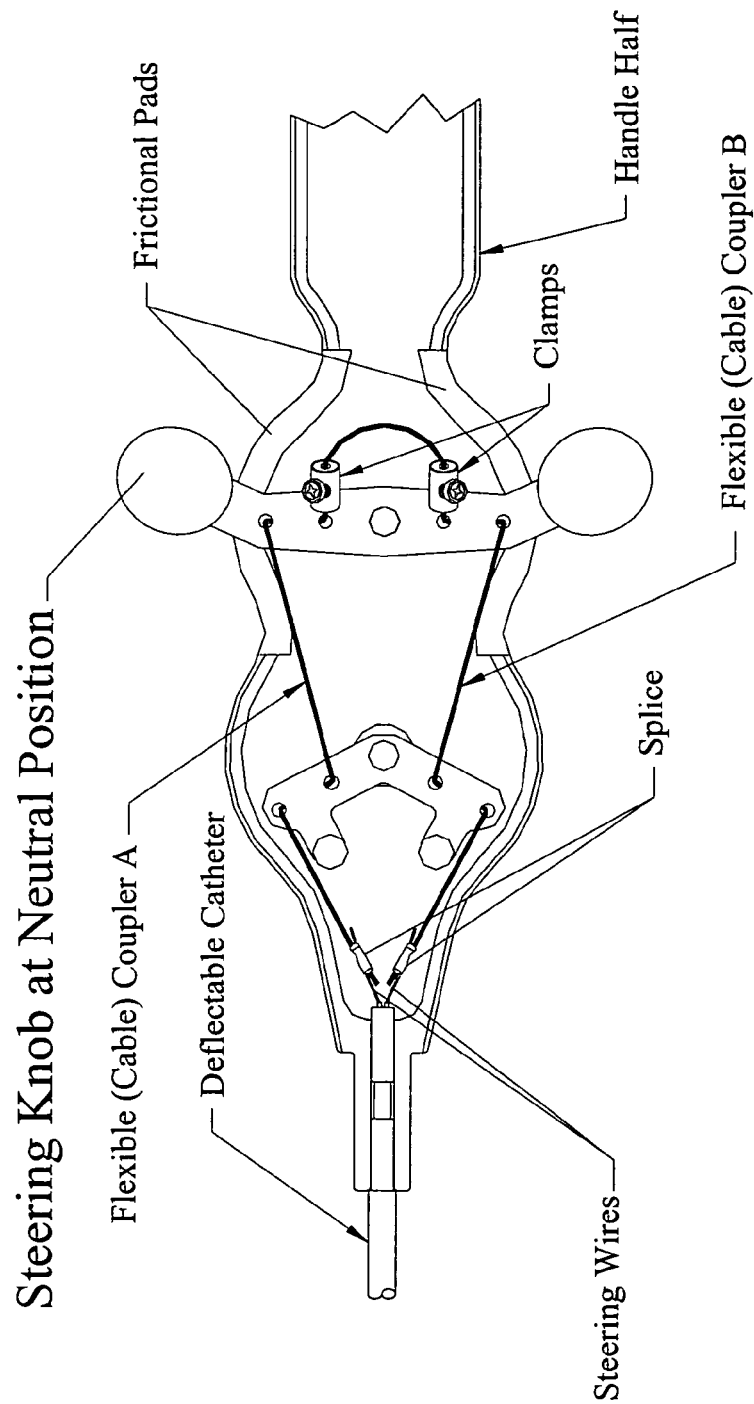
Figure 11A:
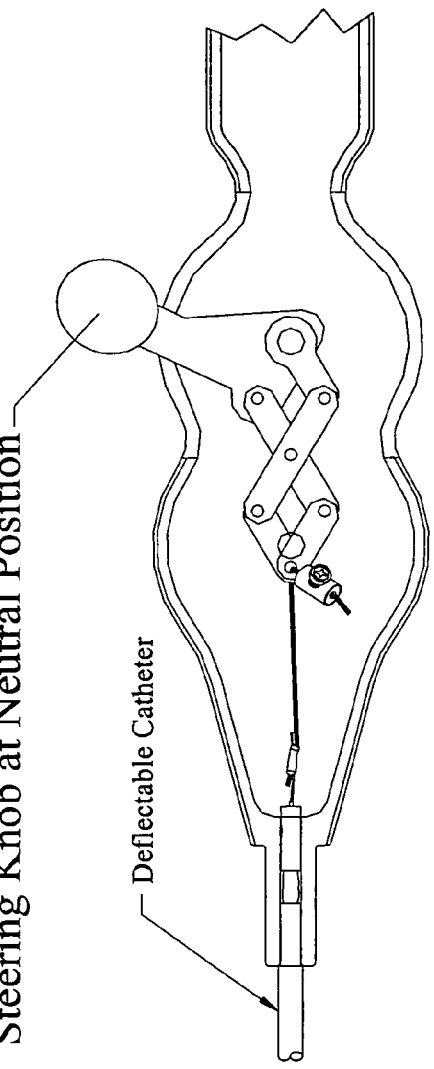
FIGS. 11A–15 are longitudinal cross-sectional views showing another alternative embodiment of a linkage steering mechanism in accordance with the present invention.
Figure 11B:
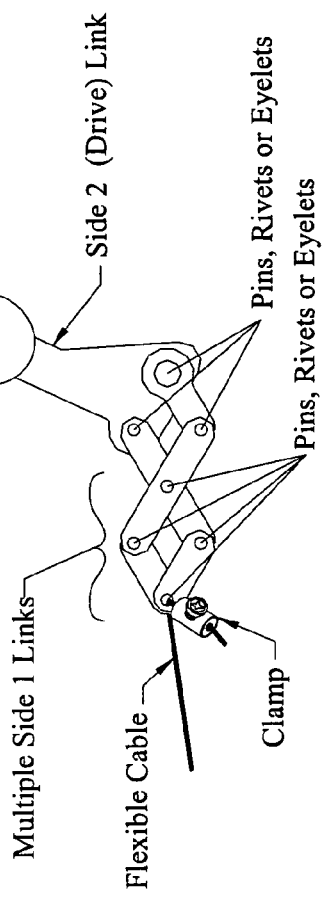
Figure 12:
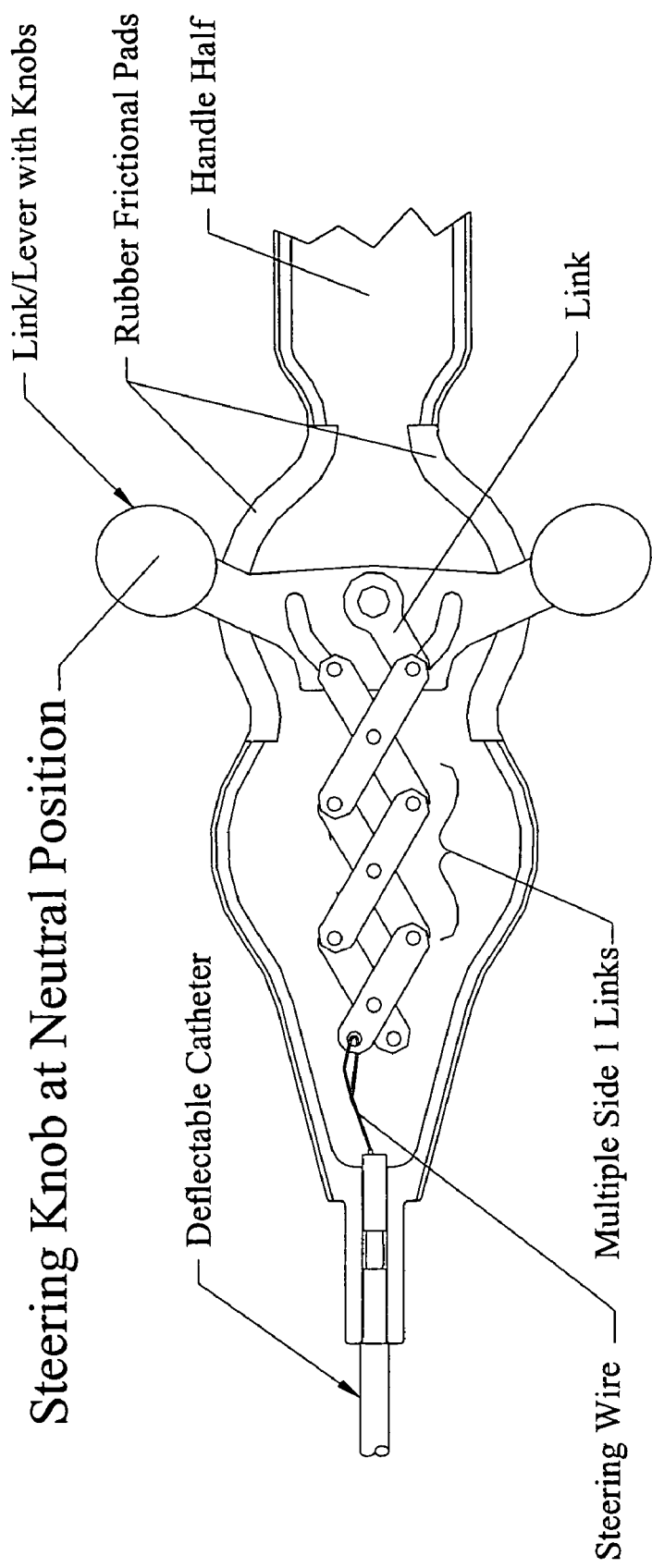
Figure 13:
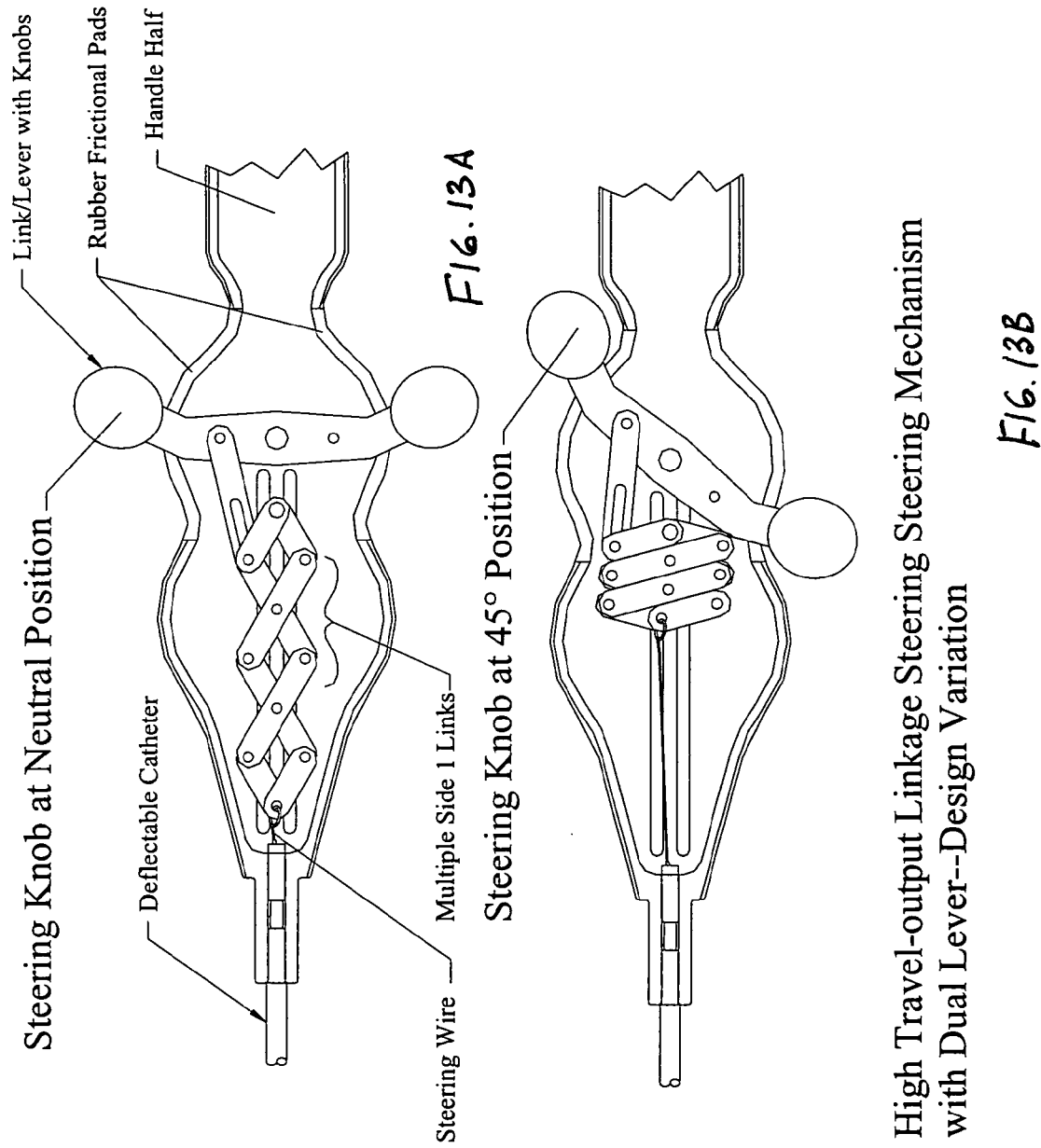
Figure 14:
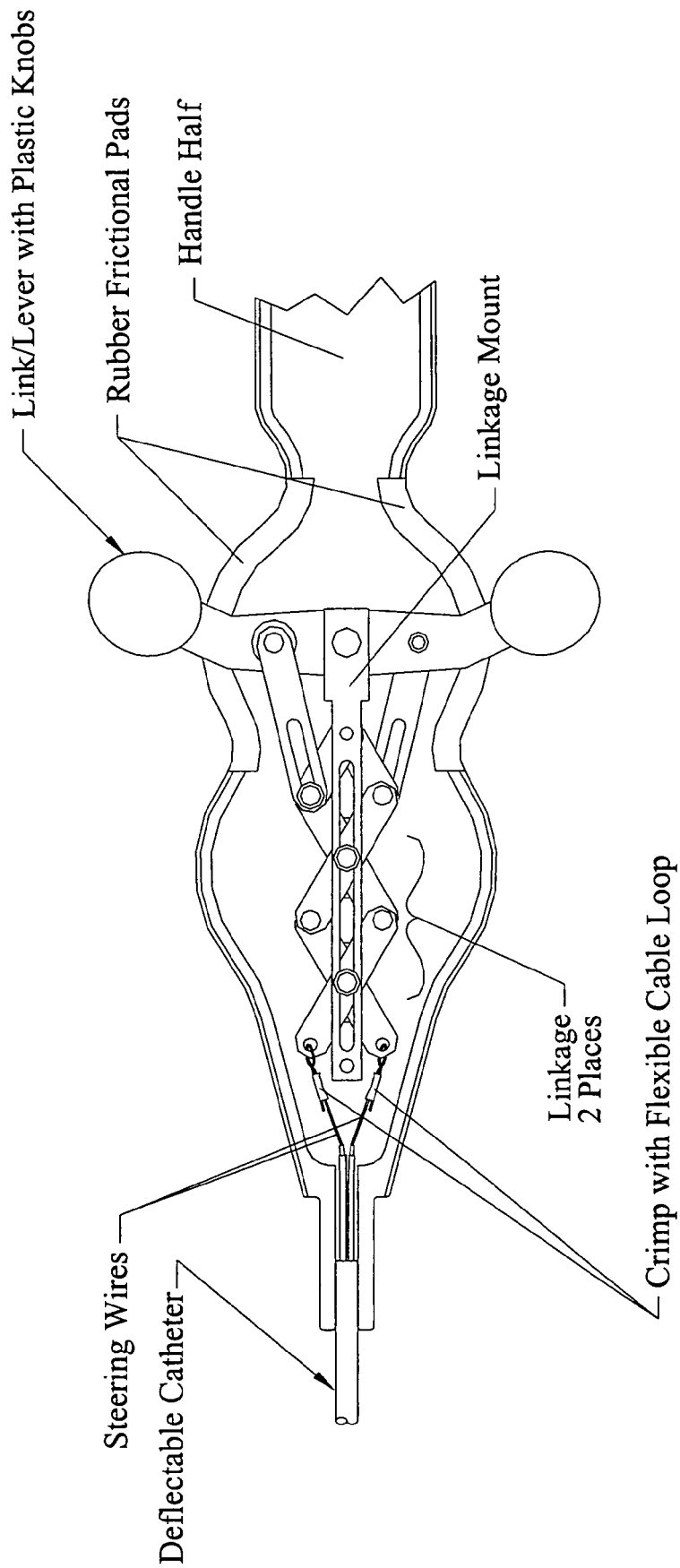
Figure 15:
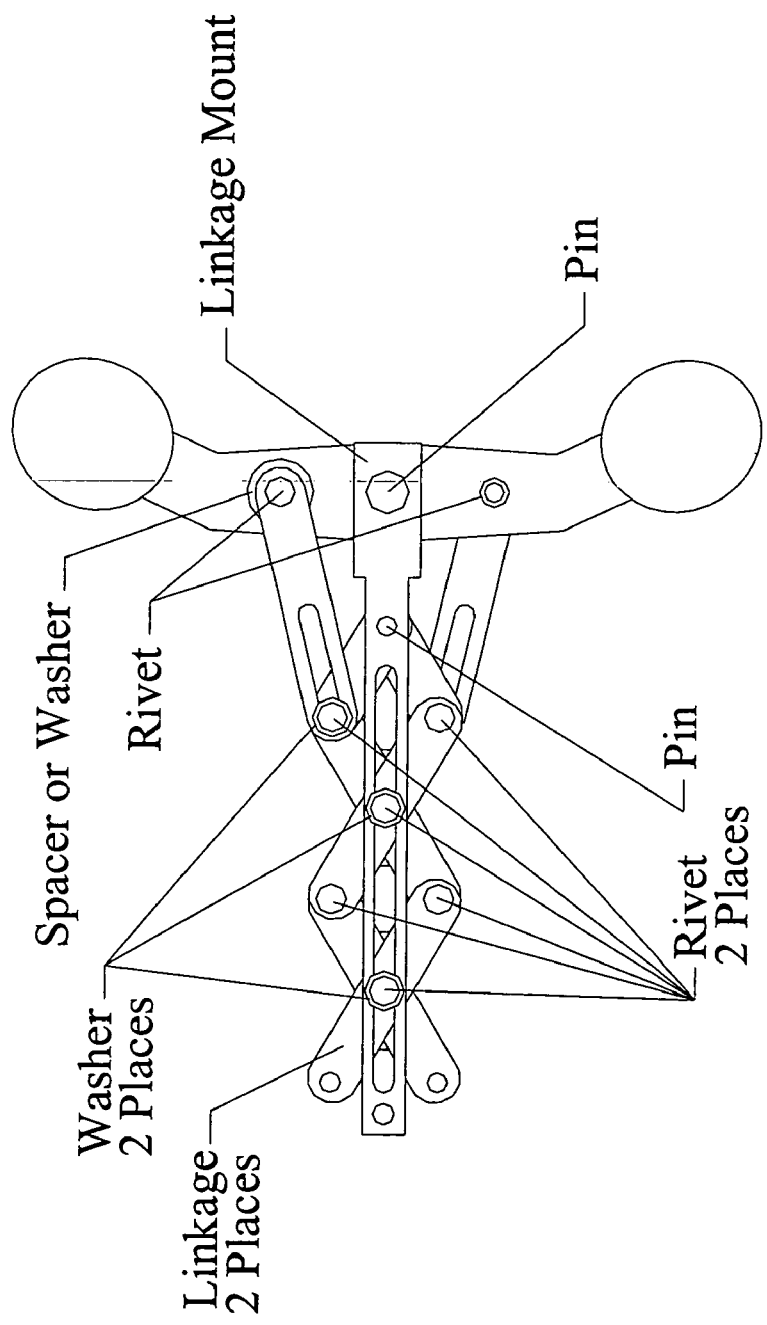
Figure 16:
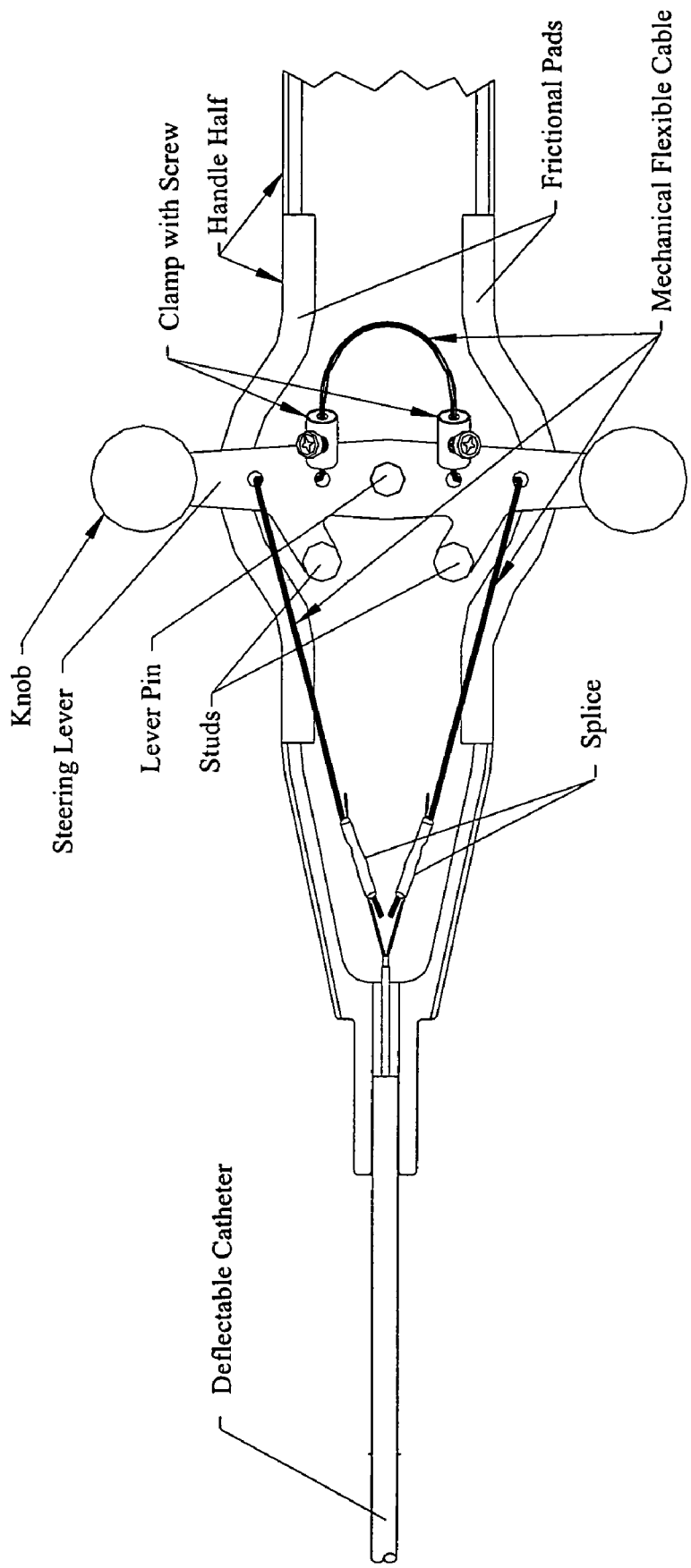
FIG. 16 is a longitudinal cross-sectional view showing another alternative embodiment of a linkage steering mechanism in accordance with the present invention.
Figure 17:
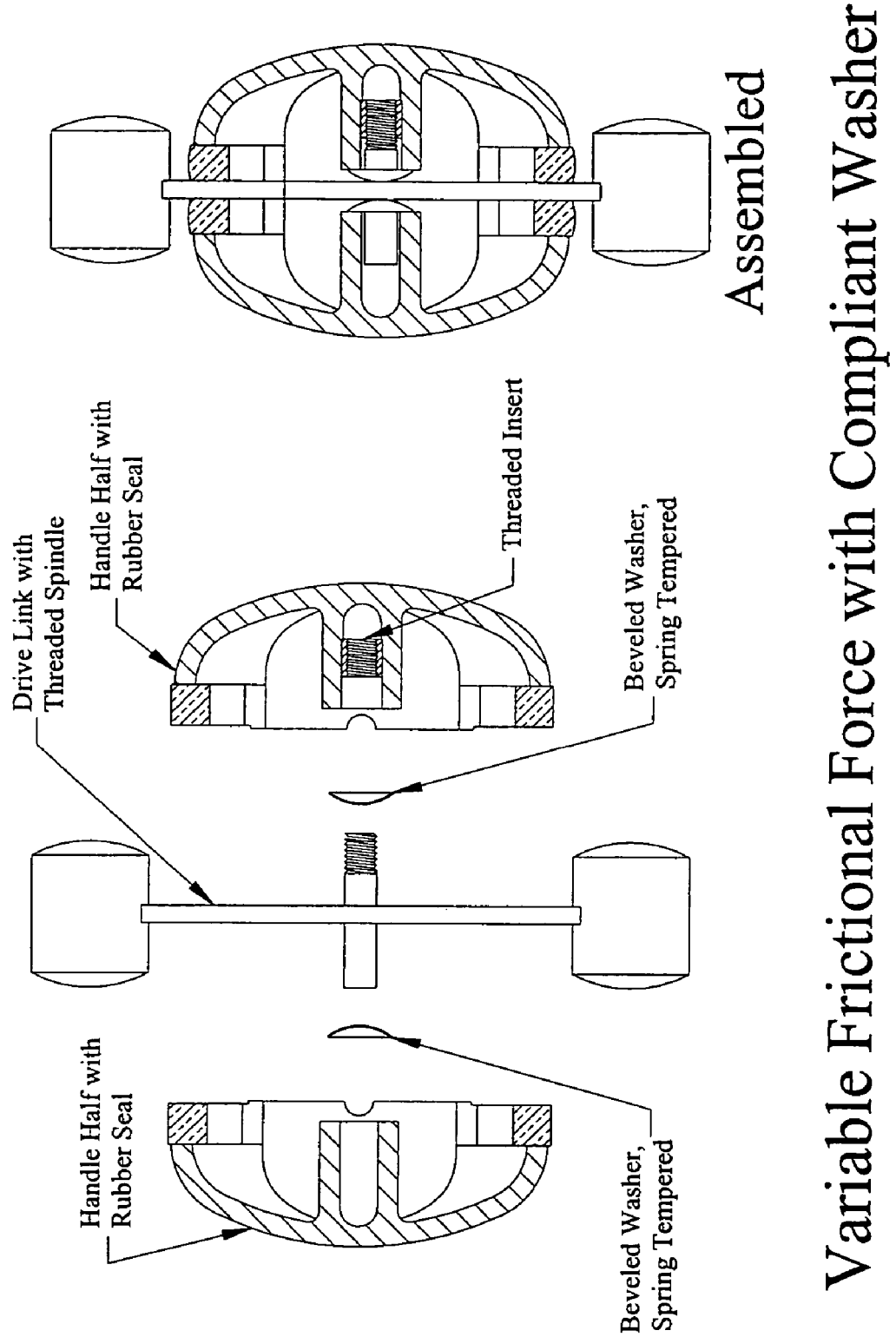
FIGS. 17 and 18 are cross-sectional views illustrating construction details in accordance with the present invention.
Figure 18:
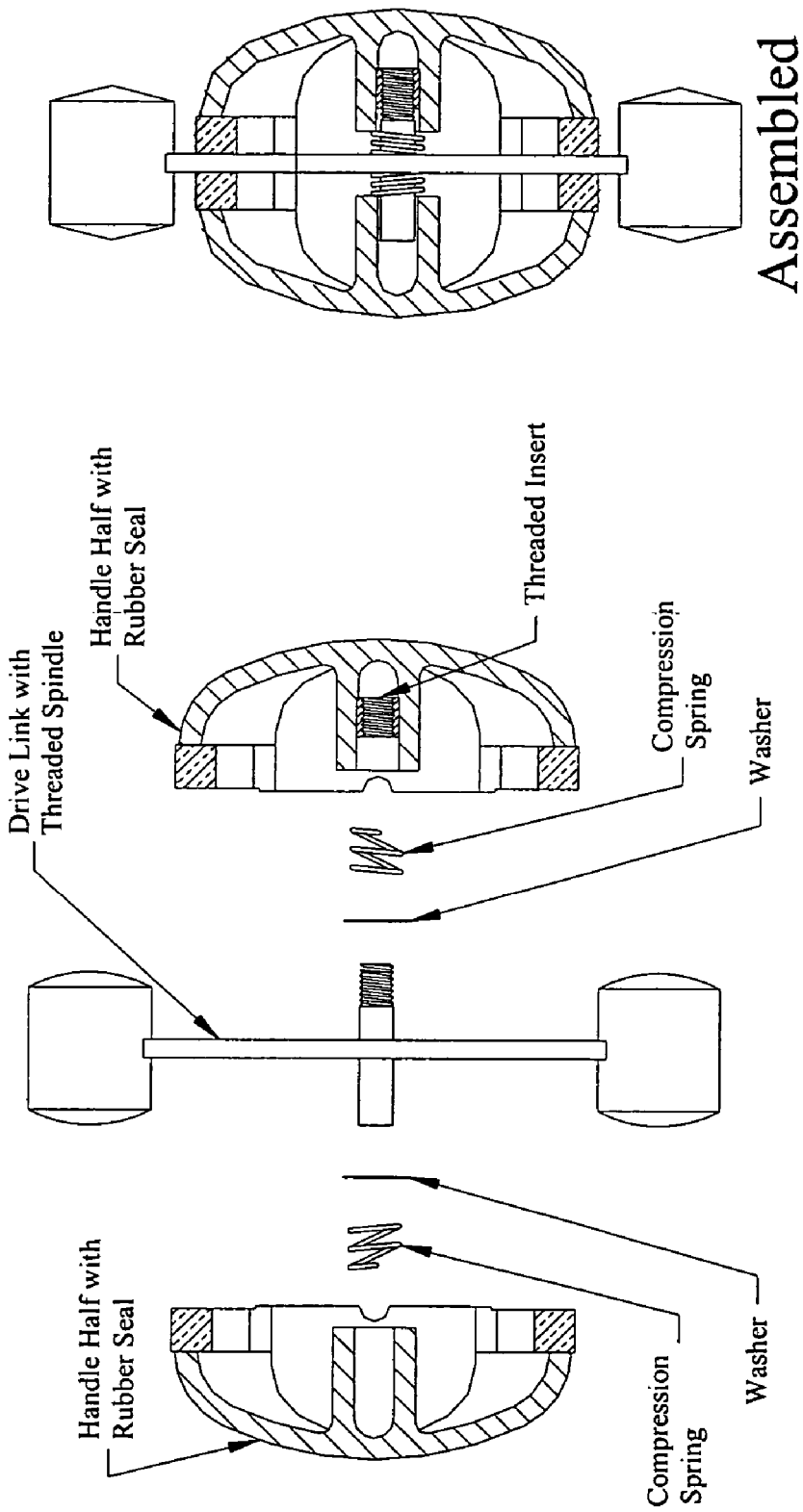

To have an ergonomic handle with an ergonomically acceptable rotary steering mechanism which, after attached to a catheter, can deflect the distal tip to 180 degrees and beyond.

DESCRIPTION OF INVENTION

A dual 4-bar linkage steering mechanism consists of four strip/rod-like prismatic or disk/sphere-like revolute side links, called, side link 1A, side link 1B, side link 2A and side link 2B; two strip/rod-like prismatic coupler links, called, coupler link A, coupler link B; and a common fixed link. In one option, the side link 1A and the side link 1B are integrated to act as a whole, and side link 2A and the side link 2B are also integrated to act as a whole. In other option, the side link 1A and the side link 1B are separate and move independently, and the side link 2A and the side link 2B are also separate and move independently. The coupler link A and coupler link B are either rigid or flexible.

The side link 1A and the side link 1B have three holes each, two of which are utilized to join them to the other links. But the side link 2A, the side link 2B, the coupler link A, the coupler link B and the fixed link have two holes each also for joining them to the other links. Additionally, the side link 1A and the side link 1B both have, as an option, an integral stud or boss that interfaces with the steering wire of a deflectable catheter. The side link 2A and the side link 2B both have a feature, which, at one of their joint holes, extends out in order to interface with and integrate to the other mechanism related parts.

By using two of its holes, the side link 1A is joined to the coupler link A and the fixed link by pins, rivets or eyelets. Through its third hole, a flexible mechanical cable with a clamp is fed and installed on the side link 1A for one of the steering wires of a deflectable catheter. The side link 2A is joined to the coupler link A and the fixed link also by pins, rivets or eyelets. A knob with ergonomic features is installed on or permanently integrated to the extended end of the side link 2A, leaving a certain amount of the extended portion for interfacing with a frictional pad on a handle.

Similarly, by using two of its holes, the side link 1B is joined to the coupler link B and the fixed link by pins, rivets or eyelets. Through its third hole, another flexible mechanical cable with a clamp is fed and installed on the side link 1B for the other steering wire of a deflectable catheter. The side link 2B is joined to the coupler link B and the fixed link also by pins, rivets or eyelets. A knob with ergonomic features is installed on the extended end of the side link 2B also, leaving a certain amount of the extended portion for interfacing with another frictional pad on the handle.

There are, as an option, additional multiple side links joined together in a crossing manner (also, called multiple side linkage) in order to obtain a high travel-output from the linkage steering mechanism. A high travel-output of the steering mechanism results in a large deflection (270 to 360 degree angles) of the distal tip of a deflectable catheter. The high travel-output linkage steering mechanism has certain design variations. Also, to obtain a high travel-output from a lever-type steering mechanism, studs are integrally added to its steering lever, as another option.

The joint pins, rivets or eyelets for the links are loose fit enough to allow all the movable links to pivot around their joints. The clamp consists of two threaded components which are fastened together to provide a clamping or radial compression force for holding the flexible mechanical cable without causing any slippage.

In one of the options, the joint between the fixed link and the side link 2A or the side link 2B or both as a whole has a threaded spindle instead of a pin, a rivet or an eyelet. The spindle is permanently integral to the side link and has threads only on its one end.

It should be noted that functionally, the side link 2A and the side link 2B or both as a whole are also called the drive links, and the side link 1A or the side link 1B or both as a whole, the driven links.

The linkage steering mechanism is installed in one of the two identical halves of a handle which has two side features where the frictional pads are mounted and a front feature where the proximal end of a deflectable catheter is mounted and the catheter's steering wires extend out. The terminal ends of the steering wires are spliced by a certain means to the flexible mechanical cable that is installed on the side link 1A and the side link 1B or both as a whole. The fixed link of the mechanism is fitted into a certain feature inside the handle half.

As an option, the handle half has an internal feature with two blind holes, which match the fixed link's joint holes in dimension and location. Using pins, the linkage steering mechanism without the fixed link is installed in the blind holes. The pin of the drive links has a compliant or spring-loaded washer between the boss of the blind hole and the drive link. The blind hole for the drive links is optionally threaded and the mechanism with the threaded spindle is installed with a compliant or spring-loaded washer between the drive link and the boss of the threaded blind hole.

At each side of the handle half, the driver link's extended portion below the knob is pressed between the frictional pads of the two handle halves when the handle halves are assembled together. The frictional pads provide an enough friction force to hold the drive link at a desired position and also form a seal around the extended portion of the link.

When the handle halves are assembled together, the compliant or spring-loaded washer compresses between the drive link and the blind-hole boss, exerting an enough friction force to hold the drive link at a desired position. This friction-hold scheme can be used instead of or in addition to the frictional pads on the handle halves. In this option, the compliant or spring-loaded washer over the drive-link pin exerts a constant frictional force throughout the angular travel of the drive link.

But, in other option, the compliant or spring-loaded washer over the threaded spindle of the drive link exerts a variable frictional force throughout the angular travel of the drive link by virtue of the threaded spindle leading into the threaded blind hole. The more the drive link travels to pull the steering wire, the more the washer compresses to exert increased frictional force. This corresponds to the fact that the more the deflectable catheter's distal tip is deflected, the more the frictional force is needed to hold the drive link of the steering mechanism.

What is claimed is:

1. A rotationally-actuated mechanism for deflectable catheters, comprising:

a handle connected to a sheath of a deflectable catheter containing at least two mechanical catheter control wires each having a distal end affixed to a distal end portion of the catheter, and a proximal end;

a linkage steering mechanism disposed within said handle and including first and second side links each having an engagement end and a first pivot end, said engagement ends extending outside of said handle for operative engagement by a user, said first pivot ends being pivotally affixed to a first pivot pin that is fixed relative to said handle, third and fourth side links each having a distal end and a second pivot end, the proximal ends of said third and fourth side links being respectively connected to a second pivot pin, and the distal ends of said third and fourth pivot links being respectively connected to the proximal ends of said control wires, and first and second coupler links respectively connecting said first side link to said third side link and said second side link to said fourth side link, whereby when said first side link is engaged and caused to rotate in a first direction about said first pivot pin, said first coupler link is translated and causes said third side link to rotate about said second pivot pin thereby causing the attached control wire to be translated within said sheath and the distal tip to be deflected in one direction from the tip's straight position to an arc angle in a plane, and wherein when said second side link is engaged and caused to rotate in the opposite direction about said first pivot pin, said second coupler link is translated and causes said fourth side link to rotate about said second pivot pin thereby causing the attached control wire to be translated within said sheath and brings the tip back to the straight position, while a further rotation of the second side link causes the tip to be further deflected in an opposite direction to an arc angle in the same plane.

2. A rotationally-actuated mechanism for deflectable catheters as recited in claim 1 wherein said first and second side links are an integrated unit attached at its midpoint to said first pivot pin.

3. A rotationally-actuated mechanism for deflectable catheters as recited in claim 2 wherein the said third and fourth side links are an integrated unit attached at its midpoint to said second pivot pin.

4. A rotationally-actuated mechanism for deflectable catheters as recited in claim 1 wherein said third and fourth side links have laterally extending arms with studs for engaging the control wires when rotated beyond a certain angle.

5. A rotationally-actuated mechanism for deflectable catheters as recited in claim 1 wherein said steering mechanism further includes a fixed link joining said first and second pivot pins.

6. A rotationally-actuated mechanism for deflectable catheters as recited in claim 1 wherein said first and second coupler links are flexible.

7. A rotationally-actuated mechanism for deflectable catheters as recited in claim 1 wherein said first and second coupler links are tortuous in configuration.

8. A rotationally-actuated mechanism for deflectable catheters as recited in claim 1 and further comprising mating clam shell configured components adapted to envelope said steering mechanism but including slots through which said first and second side links extend.

9. A rotationally-actuated mechanism for deflectable catheters as recited in claim 8 and further comprising friction pads provided along at least one edge of said slots to engage and hold in place said first and second side links.

10. A rotationally-actuated mechanism for deflectable catheters as recited in claim 1 and further comprising knobs disposed on the engagement ends of said first and second side links.

11. A rotationally-actuated mechanism for deflectable catheters, comprising:
    a handle connected to a sheath of a deflectable catheter containing at least two mechanical catheter control wires, each having a distal end affixed to a distal end portion of the catheter, and a proximal end;
    a linkage steering mechanism disposed within said handle and including
        first and second side links each having an engagement end and a first pivot end, said engagement ends extending outside of said handle for operative engagement by a user, said first pivot ends being pivotally affixed to a first pivot pin that is fixed relative to said handle, said mechanism,
        third and fourth side links each having a distal end and a second pivot end, the proximal ends of said third and fourth side links being respectively connected to a second pivot pin,
        first and second coupler links respectively connecting said first side link to said third side link and said second side link to said fourth side link, and
        at least one scissor link including first and second elongated members pivotally secured together, one end of said first member being pivotally attached to the distal end of said third link, and the opposite end thereof being connected to the proximal end of one of said control wires, and one end of said second member being pivotally attached to the distal end of said fourth link, and the opposite end thereof being connected to the proximal end of the other one of said control wires;
    whereby when said first or second side links are engaged and caused to rotate in a first direction about said first pivot pin, said first and second coupler links are translated and cause said third and fourth side links to rotate about said second pivot pin thereby causing the attached first and second members to rotate relative to each other and cause at least one of said control wires to be translated within said sheath thereby causing the distal tip to be deflected in one direction from the tip's straight position to an arc angle in a plane.

12. A rotationally-actuated mechanism for deflectable catheters as recited in claim 11 wherein said steering mechanism further includes a fixed link joining said first and second pivot pins.

13. A rotationally-actuated mechanism for deflectable catheters as recited in claim 12 wherein said fixed link extends beyond said second pivot pin and includes an elongated slot within which a pivot pin joining said first and second members slide.

14. A rotationally-actuated mechanism for deflectable catheters as recited in claim 13 and further including another scissor link including third and fourth elongated members pivotally secured together, one end of said third member being pivotally attached to the distal end of said third link, and the opposite end thereof being connected to the proximal end of one of said control wires, one end of said third member being pivotally attached to the distal end of said fourth link, and the opposite end thereof being connected to the proximal end of the other one of said control wires.

15. A rotationally-actuated mechanism for deflectable catheters as recited in claim 14 wherein a pivot pin joining said third and fourth members slide also slide within said slot in said fixed link.

* * * * *